(12) United States Patent
Sollich (10) Patent No.: US 7,954,423 B2
(45) Date of Patent: Jun. 7, 2011

(54) APPARATUS FOR DETERMINING CRYSTALLIZATION SOLIDIFICATION CURVES OF FAT-CONTAINING MASSES

(75) Inventor: Thomas Sollich, Kammwag (DE)

(73) Assignee: Sollich KG (DE)

( * ) Notice: Subject to any disclaimer, the term of this patent is extended or adjusted under 35 U.S.C. 154(b) by 1617 days.

(21) Appl. No.: 11/115,451

(22) Filed: Apr. 27, 2005

(65) Prior Publication Data
US 2005/0241491 A1 Nov. 3, 2005

(30) Foreign Application Priority Data

Apr. 29, 2004 (DE) .................. 10 2004 021 135

(51) Int. Cl.
A47J 37/12 (2006.01)

(52) U.S. Cl. ............. 99/353; 73/863; 73/864; 73/53.02; 137/561 R; 137/565.01; 374/16; 374/26; 374/27; 374/160

(58) Field of Classification Search ............ 374/16, 374/26–27, 160; 99/353; 73/863, 864, 864.64, 73/863.54, 863.85, 863.83, 863.82, 53.02; 137/561 R, 565.01
See application file for complete search history.

(56) References Cited

U.S. PATENT DOCUMENTS

| | | | | |
|---|---|---|---|---|
| 2,982,134 A | * | 5/1961 | Brown | 73/198 |
| 3,143,876 A | * | 8/1964 | Wallgren | 374/17 |
| 3,154,137 A | * | 10/1964 | Greer, Jr. | 165/267 |
| 4,631,967 A | * | 12/1986 | Welker | 73/861.25 |
| 4,889,434 A | * | 12/1989 | Sollich | 374/25 |
| 5,162,103 A | * | 11/1992 | Dechene et al. | 422/104 |
| 5,188,853 A | * | 2/1993 | Sollich | 426/231 |

(Continued)

FOREIGN PATENT DOCUMENTS

| | | |
|---|---|---|
| DE | 1124738 A | 5/1957 |
| DE | 2100689 A | 7/1972 |
| DE | 3624392 A1 | 3/1987 |
| DE | 3714951 C1 | 4/1988 |

(Continued)

OTHER PUBLICATIONS

Search Report dated Jun. 28, 2005.

Primary Examiner — Sang Y Paik
Assistant Examiner — Brett Spurlock
(74) Attorney, Agent, or Firm — Thomas, Kayden, Horstemeyer & Risley, LLP (57) ABSTRACT

An apparatus (1) for determining crystallization solidification curves of a chocolate mass (6) includes a removal location (37), a measurement chamber (9) and a melting chamber (21). The removal location (37) serves to remove a liquid sample (38) of chocolate mass (6) from a flow of liquid chocolate mass (6). The measurement chamber (9) is connected to the removal location (37) such that the liquid sample (38) of chocolate mass (6) enters the measurement chamber (9). The measurement chamber (9) includes a temperature sensor (16) serving to sense the temperature of the sample (38) of chocolate mass (6) contained in the measurement chamber (9). The measurement chamber (9) includes a cooled wall serving for solidification of the liquid sample (38) of chocolate mass (6) contained in the measurement chamber (9). The measurement chamber (9) includes a movable piston (14; 41). The melting chamber (21) is separate from the measurement chamber (9), and it serves to melt the solidified sample (38) of chocolate mass (6). The piston (14; 41) of the measurement chamber (9) is moved in a way to transfer the solidified sample (38) of chocolate mass (6) from the measurement chamber (9) into the melting chamber (21).

20 Claims, 8 Drawing Sheets

U.S. PATENT DOCUMENTS

| | | | |
|---|---|---|---|
| 6,152,019 A * | 11/2000 | Heyde | 99/348 |
| 6,164,145 A * | 12/2000 | Jaeger | 73/863.83 |
| 6,481,300 B1 * | 11/2002 | Cordry | 73/864.65 |
| 6,626,647 B2 * | 9/2003 | Herrmann | 417/269 |
| 2002/0166392 A1 * | 11/2002 | Handel | 73/863.83 |
| 2003/0180035 A1 * | 9/2003 | Jamison et al. | 392/471 |
| 2003/0236635 A1 * | 12/2003 | Priev et al. | 702/25 |

FOREIGN PATENT DOCUMENTS

| | | |
|---|---|---|
| DE | 42 09 073 A1 | 9/1993 |
| DE | 4209073 A1 * | 9/1993 |
| DE | 4316734 A1 | 12/1993 |
| GB | 2267478 A | 5/1992 |
| GB | 2267478 A * | 12/1993 |
| SU | 1068763 A * | 1/1984 |

\* cited by examiner

APPARATUS FOR DETERMINING CRYSTALLIZATION SOLIDIFICATION CURVES OF FAT-CONTAINING MASSES

CROSS REFERENCE TO RELATED APPLICATIONS

This application claims priority to co-pending German Patent Application No. DE 10 2004 021 135.3 entitled "Vorrichtung zum Erfassen von Kristallisations-Erstarrungskurven von Schokolade-und ähnlichen Fettmassen", filed Apr. 29, 2004.

FIELD OF THE INVENTION

The present invention generally relates to an apparatus for determining crystallization solidification curves of a fat-containing mass.

It is common practice in the art to also call such apparatuses "temper meters". They generally serve to determine the tempering level of a liquid chocolate mass or a similar confectionery mass containing fat. Such temper meters are often automatically operated by removing liquid samples of fat-containing mass at a removal location in adjustable time intervals. These samples are then solidified.

A temperature sensor is located approximately in the center of the sample. The temperature sensor senses the temperature and transmits it value to an evaluating unit. The evaluating unit determines and represents the course of the temperature over time. The course of the temperature provides information to a person with skill in the art about the tempering level and the tempering index of the mass, and thus about the quality of the pre-crystallized liquid chocolate.

Such temper meters may also be used in combination with a control unit to realize the required adaptation of a tempering machine, for example, when the temperature of the mass is too high or too low. In this way, well tempered chocolate is attained and may be further processed.

BACKGROUND OF THE INVENTION

An apparatus for determining crystallization solidification curves of a fat-containing mass is known from German Patent No. DE 37 14 951 C1 corresponding to U.S. Pat. No. 4,889,434. The known apparatus includes a measurement chamber being surrounded by a cooled wall. The measurement chamber is connected to a removal location (for example a tube section) for liquid pre-crystallized chocolate from which the liquid sample of chocolate is removed. The measurement chamber partly protrudes into the cross-section of flow of the tube. The measurement chamber has a cylindrical cross-section, and it is thus coordinated with a cylindrical piston being arranged in the measurement chamber to be movable in the measurement chamber. The piston carries a temperature sensor which protrudes beyond the front wall of the piston. In its retracted position, the piston protrudes into the measurement chamber to observe and sense the temperature of the solidified sample at this position. The measurement chamber is thus formed by a piston and cylinder unit which is arranged to immerse into the chocolate mass to be observed with its open front side. A drive serves to provide the stroke of the piston, the stroke being approximately coordinated with the length of the measurement chamber. A unit for removal of the solidified sample from the piston and from the temperature sensor is provided. This unit includes a mechanical crushing apparatus, especially a milling unit or a cutting unit the axis of which is aligned with the axis of the measurement chamber. The milling or cutting unit includes a shaft and a milling head driven by a motor. The milling head protrudes into the cross-section of flow of the measurement chamber from outside, and it partly locks the cross-section of flow. The shaft has to be sealed.

The known apparatus is operated as follows: Liquid chocolate mass is sucked in from the removal location and transferred into the measurement chamber by a backward stroke of the piston in the measurement chamber. The liquid sample solidifies due to the influence of the cooled wall of the measurement chamber until the entire material of the sample has solidified. To be capable of sucking in the following sample of liquid chocolate mass into the measurement chamber, the solidified sample has to be removed from the measurement chamber. This is realized by the mechanical crushing apparatus with which the solidified sample is milled. The solid particles resulting therefrom are introduced into the liquid chocolate mass which flows through the removal location. In the following, these particles are further conveyed and melted in the flow. The crushing and melting process of the solidified sample takes several minutes. The measurement chamber cannot be used during this time, meaning it is not possible to transfer another sample into the measurement chamber. Instead, one has to wait until the entire crushing and melting process of the solidified sample has been completed. Then, another sample can be taken. The period of time for checking a sample is comparatively long such that it is only possible to take samples in respective time intervals. However, a control system often requires quicker processing of samples.

The known apparatus also has the drawback of the mechanical crushing apparatus requiring its own drive. This separate drive is located outside of the removal location, and it includes rotatingly driven elements. Consequently, the milling head of the mechanical crushing apparatus, for example, it not accessible for maintenance and controlling purposes since it is located inside of the removal location. Furthermore, a seal is required for the arrangement of the drive shaft to protrude through the wall of the removal location. Furthermore, a conduit or a tube section is required. The seal is a wearing part, and it needs to be regularly replaced to prevent the chocolate mass from exiting in an undesired way.

Another drawback of the known apparatus is that it is necessary to control the drive for the piston in the measurement chamber and for the mechanical crushing apparatus in an exact way. The forward stroke of the piston with the solidified sample may not be completed before the crushing apparatus has milled the solidified sample.

SUMMARY OF THE INVENTION

The present invention relates to an apparatus for determining crystallization solidification curves of chocolate masses and other fat-containing masses or fatty masses. The apparatus includes a removal location, a measurement chamber and a melting chamber. The removal location is designed and arranged to remove a liquid sample of fat-containing mass from a flow of liquid fat-containing mass. The measurement chamber or measuring chamber is connected to the removal location such that the liquid sample of fat-containing mass enters the measurement chamber. The measurement chamber includes a temperature sensor being designed and arranged to sense the temperature of the sample of fat-containing mass contained in the measurement chamber. The measurement chamber includes a cooled wall being designed and arranged to solidify the liquid sample of fat-containing mass contained in the measurement chamber. The measurement chamber includes a movable piston. The melting chamber is designed and arranged to be separate from the measurement chamber and to melt the solidified sample of fat-containing mass. The piston of the measurement chamber is designed and arranged to be moved in a way to transfer the solidified sample of fat-containing mass from the measurement chamber into the melting chamber.

With the novel apparatus, it is possible to take and analyze an automatic series of samples of chocolate mass in comparatively short time intervals. When the term chocolate mass is used herein, it is to be understood that the same applies to other fat-containing masses and vice versa.

Before a chocolate mass is processed from the liquid state and brought to solidification, it has to be heat-treated (tempered) as it is known in the art. This means that it is first heated and thus brought into the liquid state and subsequently cooled, until the fatty fraction in the chocolate mass forms solidification crystals. This process is also known as pre-crystallization. The properties of the solidified chocolate mass differ according to the composition of the chocolate mass and the heat-treatment process used. For a good gloss, a long shelf life and fine-grained breaking of the final product, it is important that, during heat treatment, fat crystals are formed in a crystal form which is high-melting in temperature terms and that these crystal agglomerates have small dimensions and are distributed homogeneously in the chocolate mass. The degree of heat-treatment or of pre-crystallization, which is the fraction of solidified fat crystals, is also critical for the production flow. Too low a fraction (inadequate heat-treatment) causes excessively long solidification times during final cooling and can result in a poor gloss and low shelf life. Too high a solidification fraction (excessive heat-treatment) gives rise to an increased viscosity of the chocolate mass to be processed and can result in less contraction during final cooling, a poor gloss and, again, a lower shelf life.

For this reason, the temperature of the sample of chocolate mass is sensed and the solidification curves are recorded and thus captured. It is therefore possible, during a production operation, for the heat-treatment of the chocolate mass to be processed to be checked repeatedly at intervals of time to ascertain that the heat-treatment is being maintained at the desired or necessary level. Correcting measures can then also be taken on the tempering machine accordingly.

The novel apparatus includes a special melting chamber for melting the solidified sample of chocolate mass. The melting chamber and the measurement chamber are designed and arranged in a spaced apart manner. Preferably, the distance between the melting chamber and the measurement chamber at least corresponds to the diameter of the cross-section of flow at the removal location. The arrangement of the melting chamber and the measurement chamber is coordinated in a way that their axes are aligned or parallel. Usually, the measurement chamber and the melting chamber have a circular or at least partly circular cross-section.

In a first exemplary embodiment of the novel apparatus, the axes of the measurement chamber and of the melting chamber are arranged to be aligned. The stroke of the reciprocating piston is enlarged compared to the stroke of the piston of prior art apparatuses to transfer a solidified sample from the measurement chamber into the melting chamber. In this way, the cross-section of flow of the removal location is free from obstacles during the backward stroke of the piston into the measurement chamber. Thus, a following sample of liquid chocolate mass may be sucked into the measurement chamber during and with the backward stroke without the preceding sample in the melting chamber being molten. The first sample is melted in the melting chamber at the same time as the following second sample solidifies in the measurement chamber. Consequently, the cycle time of the samples which are observed in cycles is substantially reduced. This is possible since the process of solidification of the sample in the measurement chamber and the process of melting a different sample in the melting chamber at least partly take place at the same time.

A unit for retaining the solidified sample may be arranged in or at the melting chamber. This unit is active during insertion of the solidified sample into the melting chamber. The unit retains the solidified sample in the melting chamber, while the piston detaches from the solidified sample at the beginning of its backward stroke.

In a second exemplary embodiment of the novel apparatus, the piston is designed as a rotary, piston. It includes at least three chambers. These three chambers form the measurement chamber, the melting chamber and a chamber being connected to the removal location depending on the rotational position of the rotary piston. The rotary piston is driven in a housing to rotate in a clocked manner. The chambers located at the rotary piston may be designed as partly cylindrical longitudinal channels. A chamber is connected to the removal location in the transfer position. In a second position, the chamber including the liquid chocolate mass removed from the removal location is rotated to reach a position in which this chamber fulfills the function of the measurement chamber. A temperature sensor is located in the housing, and it is designed and arranged to be moved into and out off the chamber. A cooling unit is arranged in this portion of the housing. The cooling unit serves to solidify the chocolate mass by cooling it. The temperature sensor serves to sense the temperature, and a solidification curve is determined from the signals of the temperature sensor. The melting chamber is designed to be separate from the measurement chamber. The sample is melted in the melting chamber by a heating unit being arranged in the housing. The chamber of the rotary piston then rotates further on. In the third and last position, the chamber of the rotary piston gets connected to the removal location such that the sample which has been melted in the melting chamber is reintroduced into the flow of chocolate mass. A special advantage of this embodiment is la very short cycle time, meaning that it is possible to take more samples per period of time such that it is possible to record the solidification curves in reduced time intervals. Consequently, process control is even more exact.

By using a separate melting chamber, the novel apparatus prevents disadvantages resulting from mechanical crushing of the solid sample known from the prior art. Especially, reintroduction of solid particles (as they result from milling in the prior art) into the path of flow of the liquid pre-crystallized chocolate is prevented. The solid sample of chocolate may be gently and uniformly melted. It is not necessary to use especially great temperature differences. Thus, the chocolate mass is not negatively influenced. This is possible since generally the same period of time may be used for melting as well as for solidification of the following sample.

The novel apparatus may use the cross-section of flow in a tube section as the removal location. In other words, the novel apparatus is arranged in and at, respectively, this tube section. Such a tube section may be easily arranged in a conduit through which the liquid chocolate mass flows from a tempering machine into a processing machine, for example.

In a first exemplary embodiment, the measurement chamber and the melting chamber are arranged to be approximately symmetric with respect to the axis of the tube section in an opposing arrangement. The common axis of the measurement chamber and of the melting chamber is arranged to be approximately perpendicular with respect to the axis of the tube section. Since the melting chamber does not include driven elements, it is not necessary to provide a seal as it is known in the prior art for sealing the drive shaft of the mechanical crushing apparatus. Due to the fact that such a seal is not required, the novel apparatus is operationally reliable and requires less maintenance.

The measurement chamber and/or the melting chamber preferably are designed to be approximately cylindrical, meaning they have a circular cross-section. It is to be understood that the cross-section and the diameter, respectively, of the melting chamber is not smaller than the diameter of the measurement chamber. It may make sense to arrange the measurement chamber and the melting chamber to be at least substantially located outside of the cross-section of flow of the removal location to prevent a negative influence onto the cross-section of flow caused by an arrangement of the two chambers. However, it is necessary to make sure that a sample removed from the measurement chamber and to be introduced into the melting chamber does not detach from the piston too early. Otherwise, the sample could be picked up by the chocolate flowing in the cross-section of flow of the removal location. This could have a negative influence on the operation of the apparatus. To counteract this problem, a guiding cage may be arranged in the cross-section of flow of the removal location. The guiding cage serves to guide the solidified sample during its transfer from the measurement chamber into the melting chamber. The guiding cage leads and guides the solid sample on its way from the measurement chamber into the melting chamber. Even in case the solidified sample gets detached from the surface of the piston too early, it prevents the sample from being carried away by the liquid chocolate continuously flowing through the removal location. In this way, it is ensured that the solidified sample is safely and reproductively transferred into the melting chamber to be melted therein in the following. The guiding cage preferably is designed as a bush section including openings. The axis of the bush section may be aligned with the common axis of the measurement chamber and the melting chamber. The bush section preferably includes large openings such that it does not substantially influence the flow of liquid chocolate through the removal location. Instead of a bush section including openings, it is also possible to use a cage-like construction including wire sections for fulfilling the above described leading and guiding function, for example.

In the second exemplary embodiment of the novel apparatus in which the piston is designed as a rotary piston, the function of the chambers located at the rotary piston changes depending on the position of the rotary piston with respect to the housing. One advantage is that it is not required to use a guiding cage. The cross-section of the conduit is completely free in each of the standstill positions of the rotary piston. In other words, the cross-section even in the region of the removal location is not even partly locked.

The measurement chamber may include a cooling unit and the melting chamber may include a heating unit. There are a number of different possibilities of realizing these units for a person with skill in the art. Cooling may be realized by cooling water or thermoelectrically, for example by a so called Peltier element. For this purpose, the wall of the measurement chamber may be designed to be double-walled, and it may be connected to a circuit for cooling water. The temperature of the cooling water may be kept constant over time. This means that it is not necessary to change the temperature of the cooling water in intervals. The drive of the piston is sufficient to detach the solidified sample also from the inner wall of the measurement chamber. One attains the respective advantage of a constant temperature over time also with respect to the melting chamber and the connection to a double wall to constantly tempered warm water, respectively. As an advantage, it is not necessary to periodically heat or cool walls made of metal.

It is desired to retain the solidified sample contained in the melting chamber in the melting chamber during the backward stroke of the piston. For this purpose, it makes sense that the unit for retaining the solidified sample during the backward stroke of the piston includes a receiving bush in which or at which retaining elements for the inserted solidified sample are arranged. These retaining elements are designed to hold the solidified sample in a reliably way, and they make it possible to detach the piston from the rear surface of the solidified sample when the backward stroke of the piston begins. The retaining element may be designed as a ball valve being associated with the receiving bush, bent knives, barbed elements and the like. These retaining elements serve to fix the inserted solidified sample with respect to the receiving bush.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
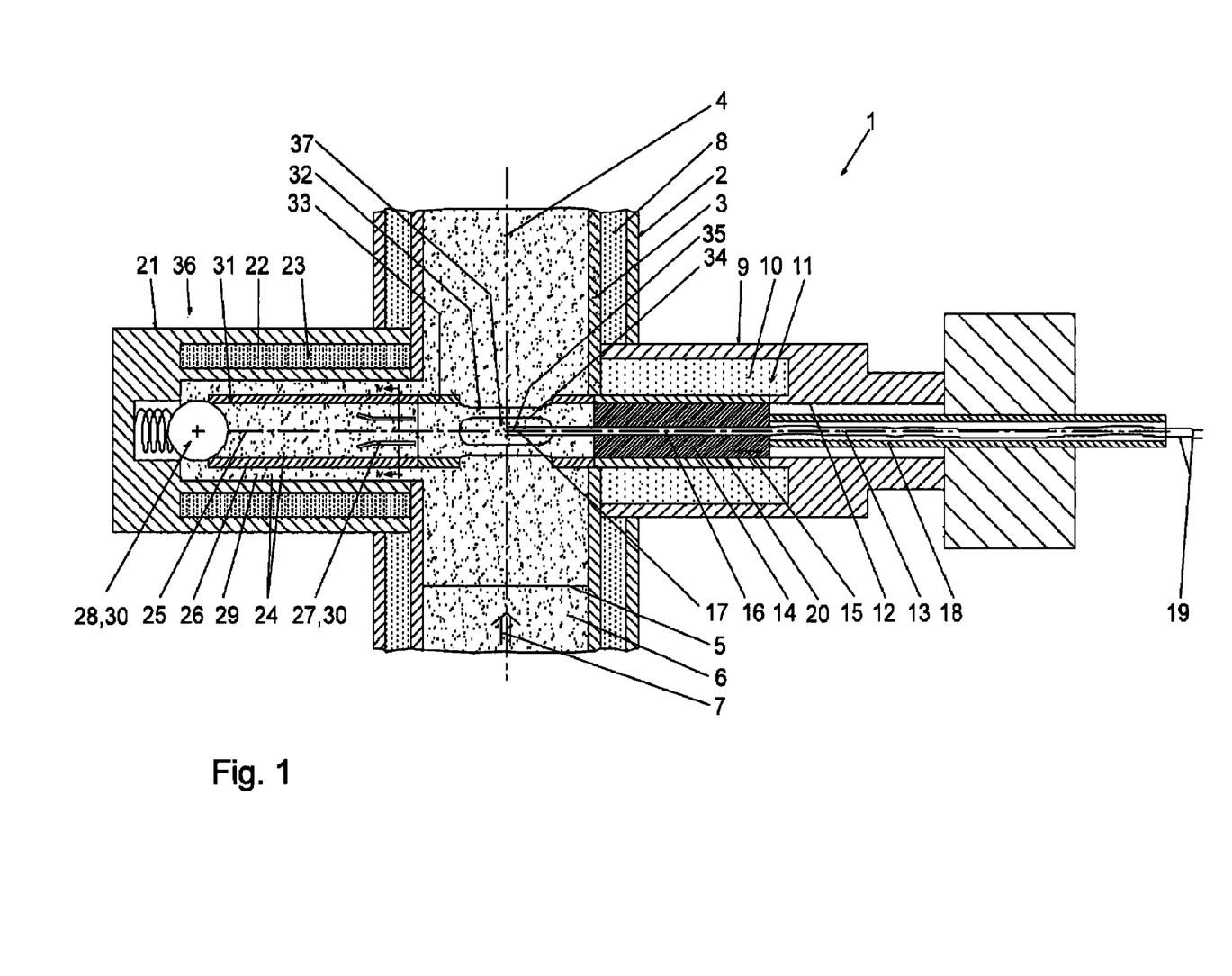
FIG. 1 is a cross-sectional view of a first exemplary embodiment of the novel apparatus in a middle position of the piston at the beginning of a sucking stroke of the piston in the measurement chamber.

Referring now in greater detail to the drawings, FIG. 1 illustrates a first exemplary embodiment of the novel apparatus 1. The apparatus 1 includes a housing 2 being designed as a tube section 3. However, the housing 2 may also have a different shape. The design of a tube section 3 is preferred since the apparatus 1 may in this way be very easily arranged in conduits by respective flange connections to the tube section 3. The housing 2 and the tube section 3, respectively, have an axis 4. In this way, a cross-section of flow 5 is realized inside of the housing 2 and of the tube section 3, respectively. In this case, the cross-section of flow 5 has a circular shape. Liquid chocolate mass 6 or a different fat-containing mass flows through the cross-section of flow 5 from below in an upward direction according to arrow 7. Usually, the flow of the chocolate mass 6 is continuous, and it is caused by a pump which is not illustrated herein. The housing 2 of the apparatus 1 usually is designed to be double-walled. A chamber 8 being formed between the two walls in this way is connected to a circuit of tempered water serving as a protecting heating system and preventing the liquid chocolate mass from changing its temperature during its flow along the length of the tube section 3.

A measurement chamber 9 is located at a side of the housing 2 and of the tube section 3, respectively, the measurement chamber 9 also being designed to be double-walled. The intermediate chamber formed between the two walls is connected to a circuit 10 for cooling water. The circuit 10 of the cooling water is operated at an adjustable but approximately constant temperature. In this way, a cooling unit 11 for the measurement chamber 9 is realized.

Figure 2:
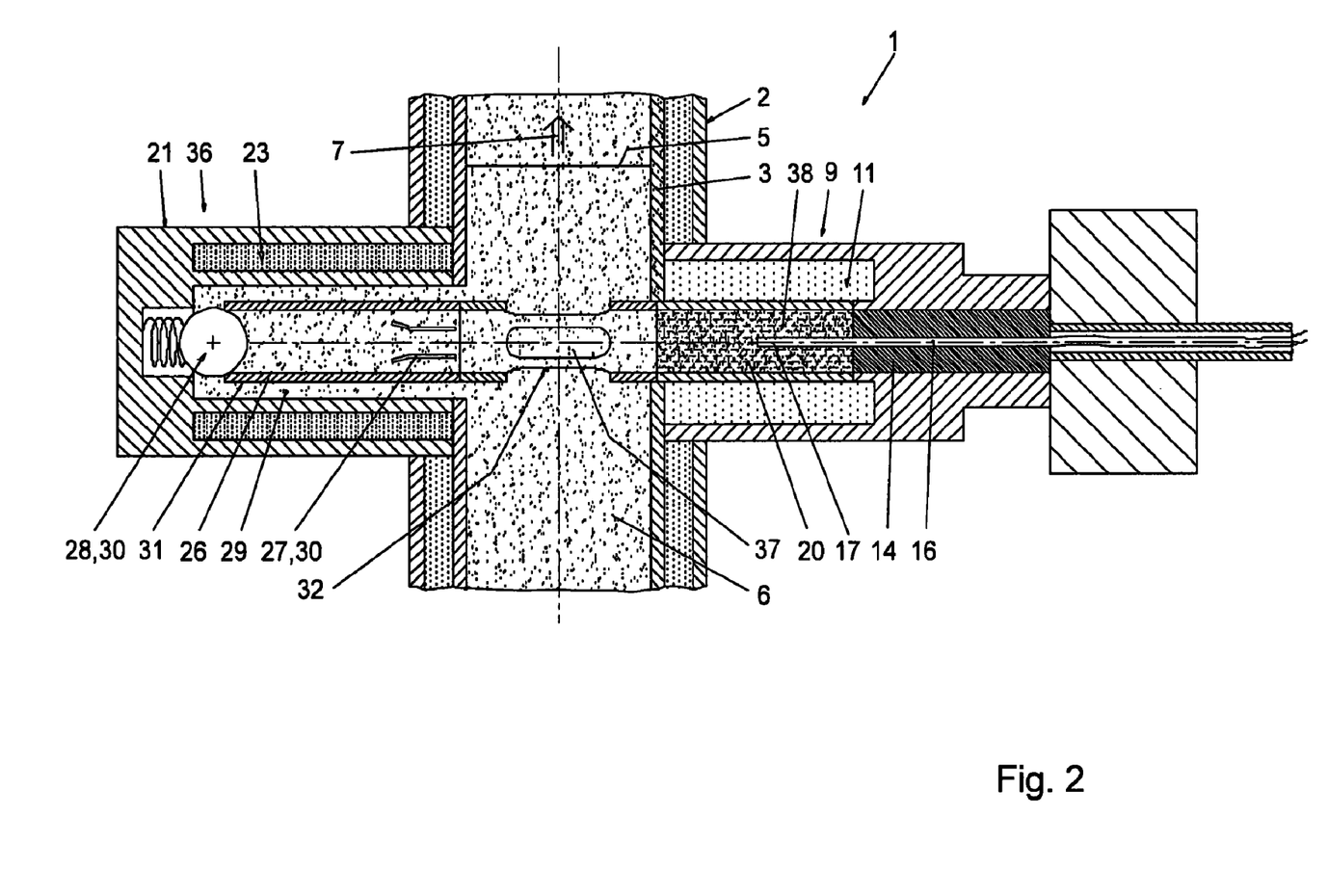
FIG. 2 is a view of the novel apparatus according to FIG. 1 in a position in which the piston in the measurement chamber has completed its backward stroke and solidification of the sucked in sample takes place.

A hollow cylinder 12 is formed inside of the measurement chamber 9, the cylinder 12 being connected to the cross-section of flow 5 of the housing 2. The cylinder 12 has an axis 13 being located to be approximately perpendicular with respect to the axis 4 of the cross-section of flow 5. A piston 14 is arranged in the cylinder 12, the piston 14 being designed and arranged to be movable in the direction of the axis 13 according to arrow 15 by a drive (not illustrated). In other words, the piston 14 has a forward stroke and a backward stroke. The piston 14 includes a temperature sensor 16. The temperature sensor 16 is centrically arranged in the piston 14, and its front end 17 freely protrudes out off the piston 14. The piston 14 includes a piston rod 18 serving to drive the piston 14 and the temperature sensor 16, respectively. Connecting lines 19 of the temperature sensor 16 protrude through the piston rod 18, and they are connected to a unit (not illustrated) for recording and evaluating the signals received by the temperature sensor 16. Next to the cross-section of flow 5, a front portion of the cylinder 12 forms a measurement chamber 20. The measurement chamber 20 is approximately located at the place where the movable piston 14 is illustrated in FIG. 1. When the piston 14 reaches its backward dead center (as illustrated in FIG. 2), the measurement chamber 20 is fully visible.

A melting chamber 21 is arranged at the side of the housing 2 and of the tube section 3, respectively, opposite to the measurement chamber 9. The melting chamber 21 is designed to be double-walled. The resulting intermediate chamber between the two walls is connected to a circuit 22 for warm water. In this way, a heating unit 23 is realized. Other exemplary embodiments of the heating unit 23 are possible. For example, the heating unit 23 could also be designed to be electrical. The circuit 22 is also operated with water, in this case warm water. The temperature is adjustable, and it may be constant during the sample period. The chosen temperature has to be sufficient to melt a solidified sample of chocolate mass. On the other hand, the temperature has to be chosen to be sufficiently low to make sure not to negatively influence the properties of the chocolate mass 6 flowing through the cross-section of flow 5. A melting room 24 is formed inside of the melting chamber 21. As the measurement chamber 20, the melting room 24 may also have a circular cross-section. Preferably, it has a diameter which is slightly greater than the diameter of the measurement chamber 20 and an intermediate guiding cage 32, respectively, to make it possible to transfer a solidified sample from the measurement chamber 20 into the melting room 24. Taking into account that chocolate masses contract during solidification, the measurement chamber 20, the guiding cage 32 and a receiving bush 26 located inside of the melting room 24 may have approximately the same inner diameter. For example, this may be realized by a continuous tube section. The melting chamber 21 and the melting room 24, respectively, include an axis 25 being aligned with respect to the axis 13 of the measurement chamber 20. The receiving bush 26 is arranged in the melting room 24 in a stationary manner. Bent knives 27 are associated with the stationary receiving bush 26. It is also possible to use barbed elements. Alternatively or additionally, the receiving bush 26 may include a ball valve 28 being located at the end of the receiving bush 26 facing away from the cross-section of flow 5. As illustrated, the ball valve 28 includes a ball and a spring. The receiving bush 26 may include openings (not illustrated). The outer diameter of the receiving bush 26 is less than the inner diameter of the melting room 24 to attain an overflow channel 29 for backflow of melted chocolate mass 6 into the cross-section of flow 5. The knives 27, the barbed elements and/or the ball valve 28 form retaining elements 30. In combination with the receiving bush 26, a unit 31 for stopping or retaining an inserted solidified sample 38 in the melting chamber 21 is realized. The elements of the unit 31 for stopping a solidified sample are to be understood as examples. It is to be understood that a person with skill in the art may also use other embodiments.

The guiding cage 32 is arranged between the measurement chamber 9 and the melting chamber 21 in a stationary manner. The guiding cage 32 includes a bush section 33 including large openings 34. The guiding cage 32 serves to guide a solidified sample during its transfer from the measurement chamber 20 into the melting room 24 and to thus prevent floating of the sample in the cross-section of flow 5 according to arrow 7. The guiding cage 32 could also be designed as a light wire construction. Usually, it is connected to the receiving bush 26, and it is supported on the receiving bush 26, respectively. It could also be designed as one piece with the receiving bush 26. The guiding cage 32 and the bush section 36, respectively, have an axis 35. The axis 35 is aligned to the axes 13 and 25 such that a common axis is formed in this way.

The stroke of the piston 14 is chosen such that the piston 14 may be moved to reach the end of the guiding cage 32 and the beginning of the receiving bush 26 of the melting chamber 21, respectively, to transfer a solidified sample from the measurement room 20 of the measurement chamber 9 into the receiving bush 26 of the melting chamber 21. The piston 14 with its piston rod 18 and the associated drive substantially form the movable elements of the apparatus 1. The melting chamber 21 including the melting room 24, the retaining elements 30 and the heating unit 23 together with additional elements form a unit 36 for removing a solidified sample 38 from the piston 14 and the temperature sensor 16 as well as for melting and reheating the melted chocolate mass into the cross-section of flow 5.

Preferably, the apparatus 1 is operated in a continuous way. This means that samples of chocolate mass 6 are taken from the cross-section of flow 5 in predetermined intervals, they are solidified and melted afterwards. Such a cycle occurs as follows:

A removal location 37 is located in the cross-section of flow 5 of the housing 2. Liquid chocolate mass 6 constantly flows through the removal location 37. The removal location 37 may be located in the region of the large openings 34 of the guiding cage 32, or in the wall portion of the housing 2 facing the measurement room 20 of the measurement chamber 9, for example. The latter arrangement is especially suitable if the guiding cage 32 is not supported at the wall of the tube section 3 at the measurement room 20, meaning if the guiding cage 32 is designed to be slightly shorter. However, the measurement room 20 is connected to the cross-section of flow 5 to realize a sucking stroke of the measurement chamber 9 during a backward stroke of the piston 14 when moving from the position illustrated in FIG. 1 towards the position illustrated in FIG. 2. Due to this sucking stroke, the measurement room 20 is filled with fresh liquid chocolate mass 6. In the following, this chocolate mass 6 is solidified due to the effect of the cooling unit 11. In this way, the solidified sample 38 is formed in the measurement room 20. The solidified sample 38 is a cylindrical element of solid chocolate mass. The process of solidification is sensed by the temperature sensor 16 the front end 17 of which is arranged at a representative position in the measurement room 20 and in the solidified sample 38, respectively. The march of temperature of the sample 38 is recorded and evaluated in a way known in the art. Thus, this evaluation for determining crystallization and solidification curves of the mass is not described herein in greater detail.

Figure 3:
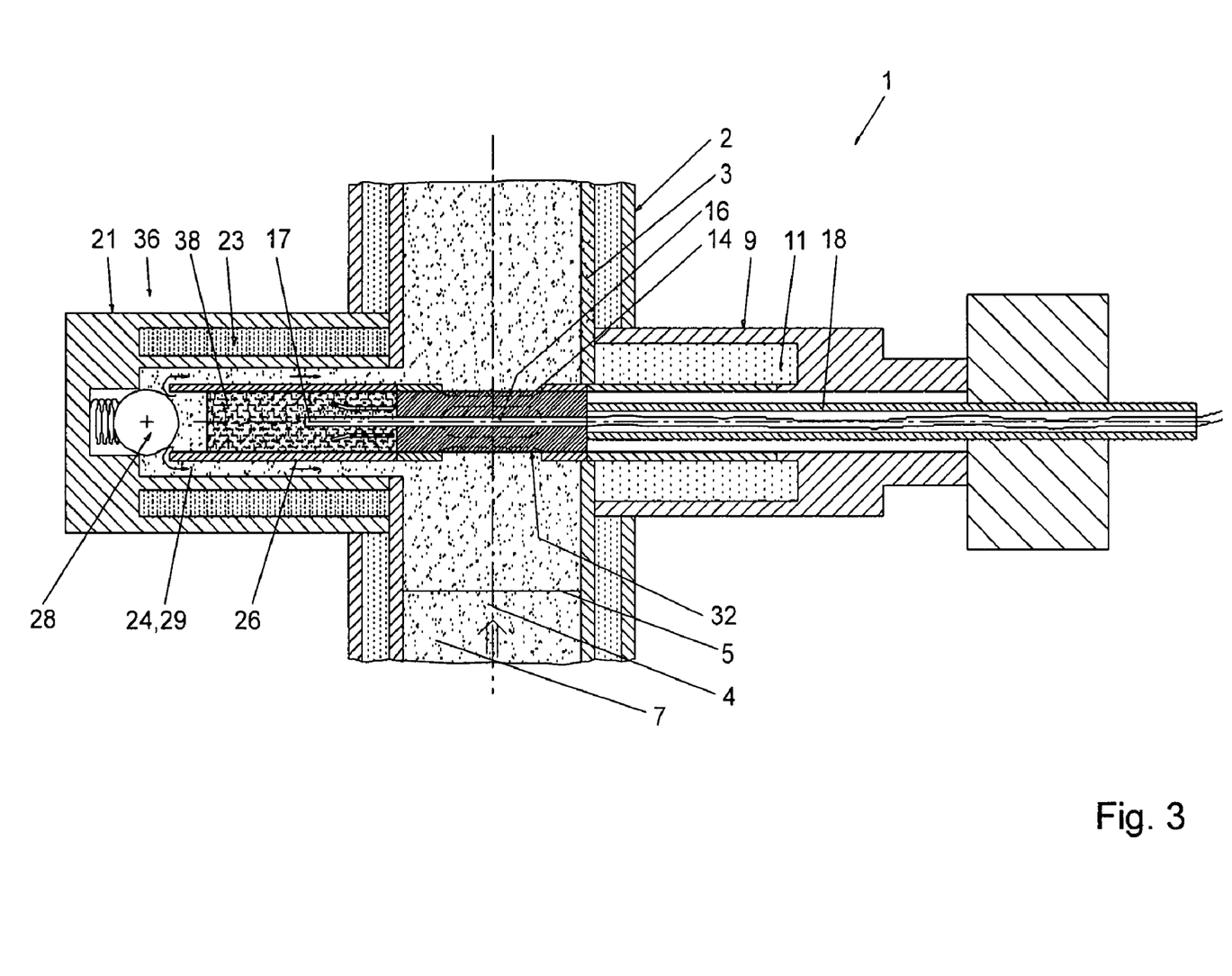
FIG. 3 is a cross-sectional view of the exemplary embodiment of the novel apparatus according to FIGS. 1 and 2 just before complete transfer of the solidified sample into the melting chamber.

After complete solidification of the sample 38, the drive of the piston 14 is actuated such that the piston 14 fulfills its forward stroke. This procedure is to be best seen from a comparison of the position illustrated in FIG. 2 with the one illustrated in FIG. 3. At the beginning of the forward stroke of the piston 14, the circumferential surface of the sample 38 detaches from the inner wall of the measurement room 20, while the front wall of the sample 38 facing the piston 14 sticks to the piston 14. During the forward stroke, the solidified sample 38 at first reaches the region of the guiding cage 32. The sample 38 is guided through the hollow room of the guiding cage 32. The guiding cage 32 prevents the sample 38 from getting detached from the front surface of the piston 14. If the sample 38 was detached in the region of the cross-section of flow 5, it could be picked up by the chocolate mass 6 flowing in the direction of arrow 7 in a way that it would not reach the melting chamber 21. This is to be prevented either by the arrangement of a guiding cage 32 or by respective enlargement of the contact surface in the front portion between the piston 14 and the sample 38. The guiding cage 32 with its large openings 34 does not have a substantial negative effect onto the flow in the cross-section of flow 5 such that its arrangement makes sense. The guiding cage 32 is coordinated with the receiving bush 26 of the melting chamber 21, and it is sized such that the solidified sample 38 is moved into the receiving bush 26 (FIG. 3) during continued forward movement of the piston 14. The molten chocolate masses being located in the receiving bush 26 is pushed into the overflow channel 29 and into the cross-section of flow 5 by opening the ball valve 38 (see the arrows in FIG. 3). The retaining elements 30 and the unit 31 for retaining the solidified sample 38 in the receiving bush 26 and in the melting chamber 21, respectively, are then actuated. The solidified sample 38 may be kept in place to a certain extent by closing the ball valve 28 after the piston 14 has reached the forward dead center of its stroke, meaning when the piston 14 begins its backward stroke. This effect is especially substantial if the receiving bush 26 does not include openings located at its cylindrical wall. Alternatively or additionally, the bent knives 27 or other barbed elements located in the region of the receiving bush 26 may have a positive effect onto retention of the solidified sample 38 inserted in the receiving bush 26. Thus, the solidified sample 38 may get detached from the front surface of the piston 14. The solidified sample 38 is thus located in the melting chamber 21, and it remains there until the piston 14 fulfills its backward stroke. As soon as the piston 14 reaches its position illustrated in FIG. 1, another sucking stroke starts and a following sample of liquid chocolate mass 6 is sucked into the measurement room 20. While measurement takes place and the solidification curve is recorded, the solid sample 38 of the previous cycle is melted in the melting chamber 21 to reach the molten condition. During transfer of the solidified sample 38 of the second cycle, the molten heated chocolate mass of the previous sample 38 is dislocated during the transfer, and it flows into the cross-section of flow 5. In this way, it is imaginable that solidification of a following sample 38 and melting of the previous sample 38 may take place to have a overlap in time. This overlap may be fully or partially used. Anyway, the clock interval of such automatic monitoring of a flowing chocolate mass is substantially reduced.

Figure 4:
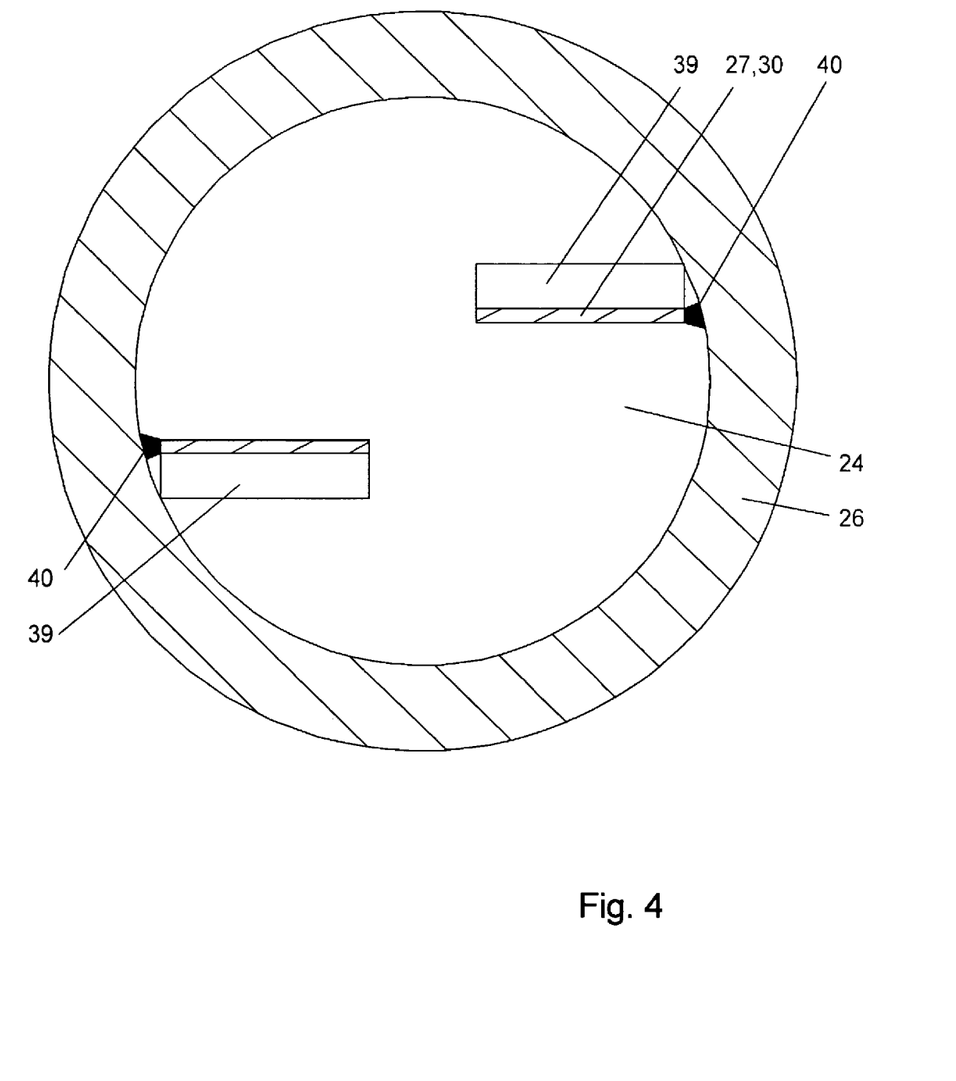
FIG. 4 is a sectional view approximately along line IV-IV in FIG. 1 illustrating the retaining elements.

FIG. 4 illustrates some details of the unit 31 for retaining a solidified sample 38 being located in the receiving bush 26, but not the sample 38 itself. Two knives 27 are located at the inner circumference of the receiving bush 26 in the illustrated relative position. As it may also be seen in FIG. 1, the knives 27 include bent resilient ends 39. The other ends of the knives 27 may be designed to be beveled to make sure that the knives 27 cut into a solidified sample 38 during insertion of the solidified sample 38. The knives 27 are fixedly connected to the inner circumference of the receiving bush 26 by weld seams 40. During continued insertion, the bent knives 27 reach an elongated shape, and they thus act as retaining elements 30. It is to be understood that there also are other possibilities of realizing and designing the retaining elements 30. For example, it is possible to alternatively arrange a plurality of short thin knife-like ribs. These ribs begin at the inner circumference of the receiving bush 26, and they extend in a radial direction, and they are continuous in an axial direction. These ribs cut into the circumference of the solidified sample 38 during its insertion.

The second exemplary embodiment of the novel apparatus 1 is illustrated in FIGS. 5 to 8. This embodiment of the apparatus 1 also includes a housing 2 including a tube section 3. A conveying conduit for chocolate mass 6 is connected to the tube section 3 such that chocolate mass 6 flows through the cross-section of flow 5 in the housing 2 in a direction perpendicular with respect to the plane of illustration of FIG. 5. The tube section 3 has an axis 4.

Figure 5:
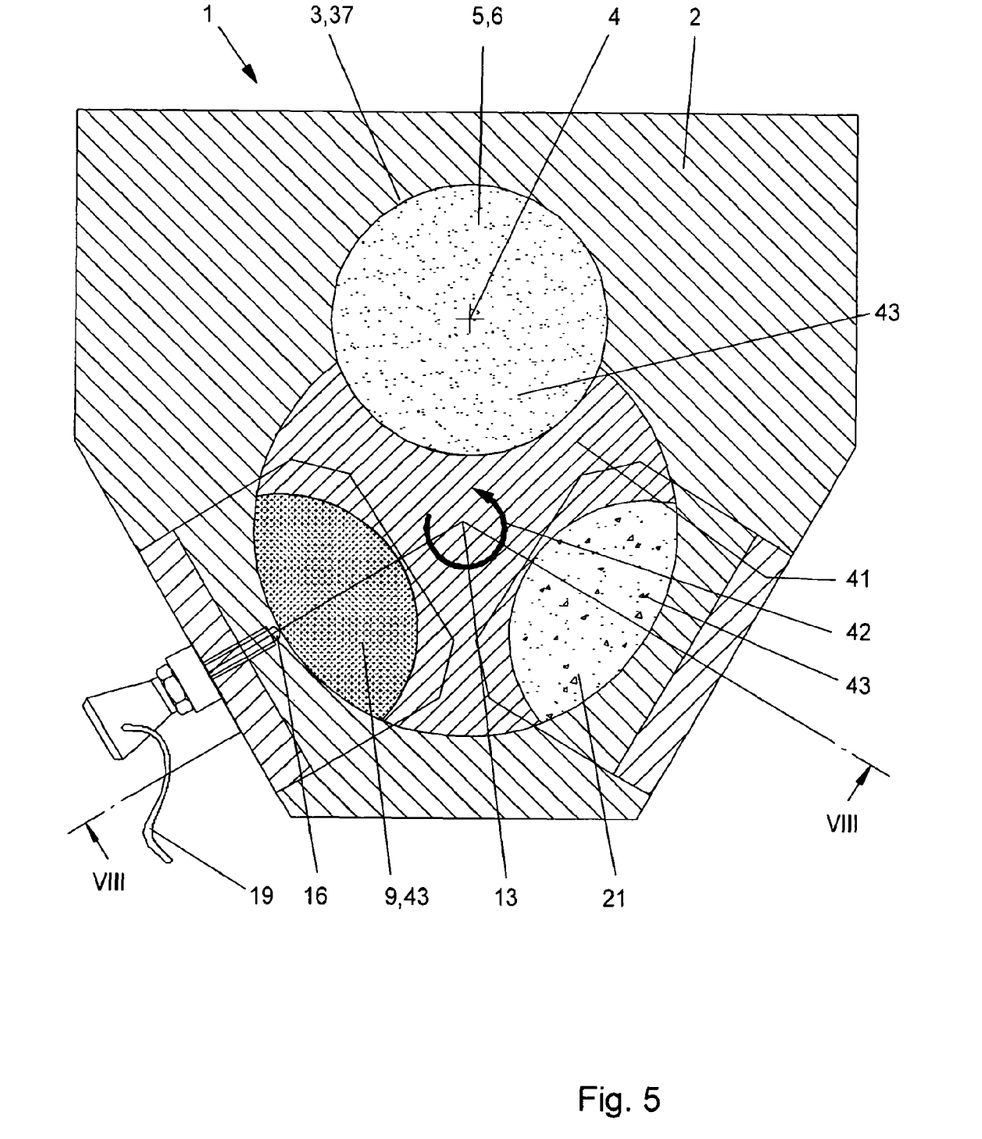
FIG. 5 is a sectional view of a second exemplary embodiment of the novel apparatus.

In this exemplary embodiment of the apparatus 1, the piston is designed as a rotary piston 41 the axis 13 of which is aligned with and spaced apart from the axis 4 of the cross-section of flow 5 in a way that the cross-section of flow 5 is "cut" by the rotary piston 41. The rotary piston 41 is rotated in a clockwise manner according to arrow 42 to reach the three positions. The rotary piston 41 includes at least three chambers 43 of the same division. The chambers 43 have identical designs, and they include a portion of a cylinder which in this case adds to the cross-section of flow 5. The three chambers 43 change depending on the rotational position, and they fulfill the function of a removal chamber, a measurement chamber 9 and a melting chamber 21. The temperature sensor 16 is designed to be moved into the region of the measurement chamber 9 and out off the measurement chamber 9, respectively, and it is supported in the housing 2 of the apparatus 1. The housing 2 includes cooling channels (not illustrated) in the region of the measurement chamber 9. A cooling medium flows through the cooling channels such that the liquid chocolate mass solidifies in the region of the measurement chamber 9. In a corresponding way, channels are also located in the region of the melting chamber 21 in the housing 2, the channels being connected to a heating circuit (not illustrated).

It is to be seen that the temperature sensor 16 in the position according to FIG. 5 is located outside of the measurement chamber 9 to make it possible to drive the rotary piston 41 in a clockwise continued manner.

Figure 6:
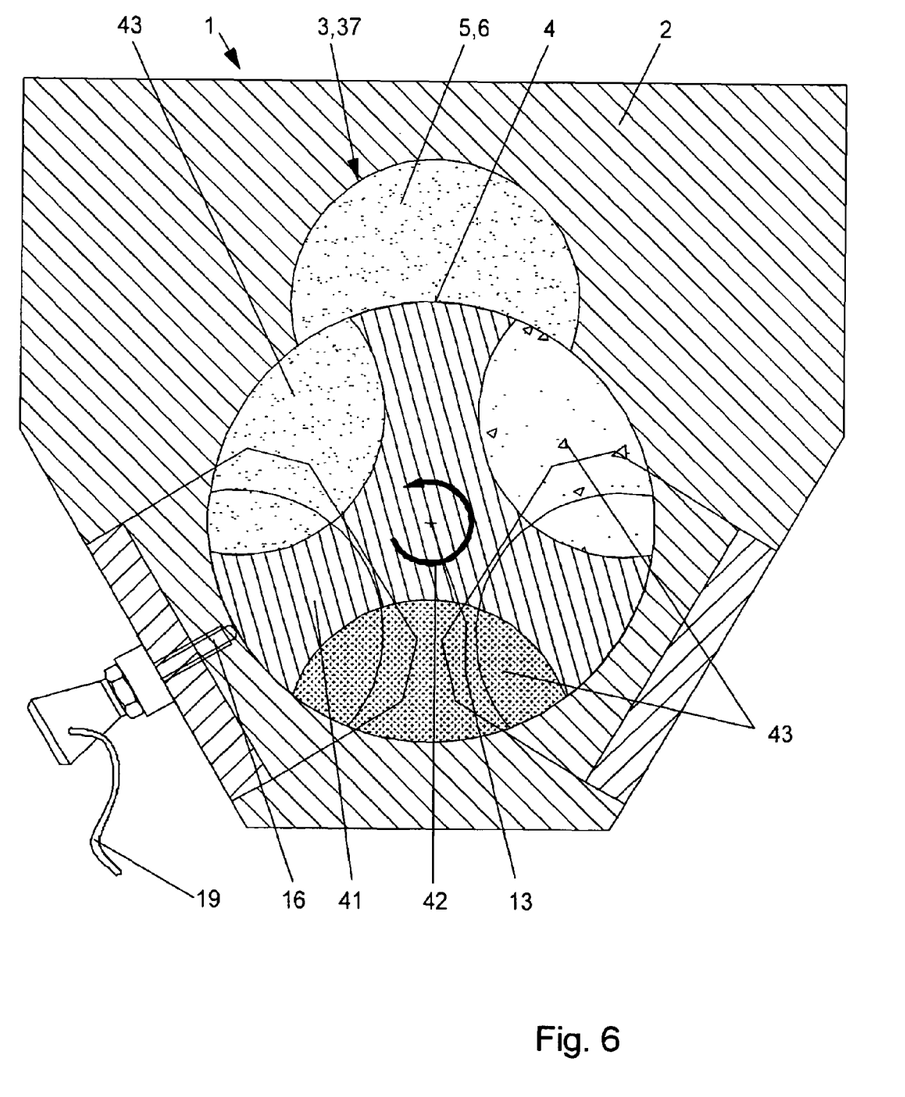
FIG. 6 is a sectional view similar to FIG. 5 but in a position further rotated by half a division.

FIG. 6 illustrates the position of the elements after half a rotation, meaning in an intermediate position. Again, the temperature sensor 16 is still located outside of the measurement chamber 9.

Figure 7:
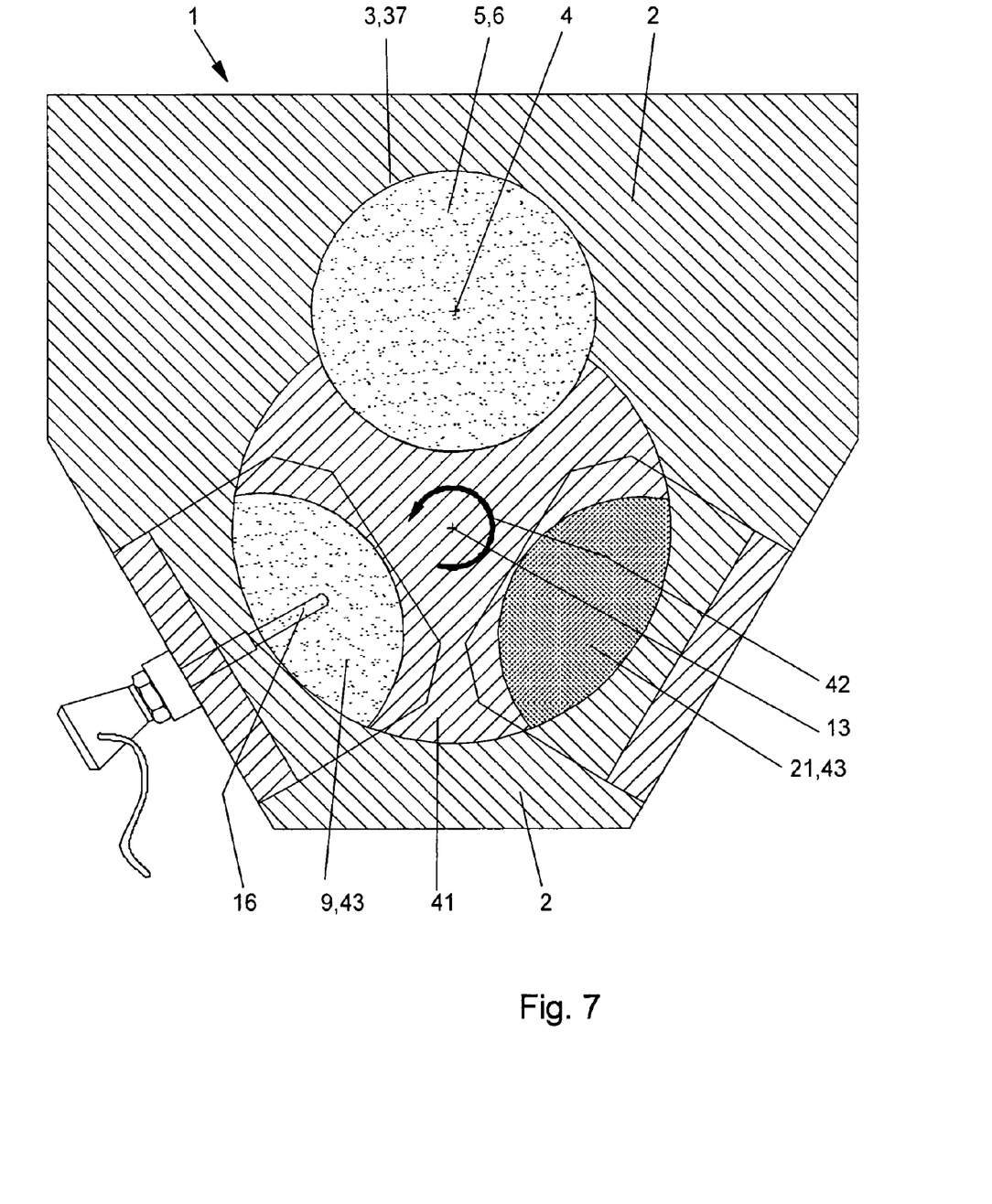
FIG. 7 is a sectional view similar to FIG. 5 but further rotated by one division.

FIG. 7 illustrates the position of the chambers 43 being reached after a full rotation. The chamber 43 which is the upper chamber in FIG. 5 has removed liquid chocolate mass from the cross-section of flow 5. It has transferred the chocolate mass into a portion in which the chamber 43 fulfills the function of the measurement chamber 9. The temperature sensor 16 is moved into the still liquid chocolate mass in the region of the measurement chamber 9 (FIG. 7). Due to cooling of the chocolate mass, the chocolate mass solidifies. The solidification curve is recorded via the connecting line 19. At the same time, the previous sample being located in the preceding chamber 43 is melted in the melting chamber 21 to reach the molten condition. It is easily imaginable that the molten chocolate mass is reintroduced into the cross-section of flow 5 when further rotating the rotary piston 41 about a full division. Also, it is to be realized that the cross-section of flow 5 is free from any obstacles and that the flow of chocolate mass 6 is not negatively influenced with the exception of the intermediate positions according to FIG. 6. However, these positions are only active for a short period of time.

Figure 8:
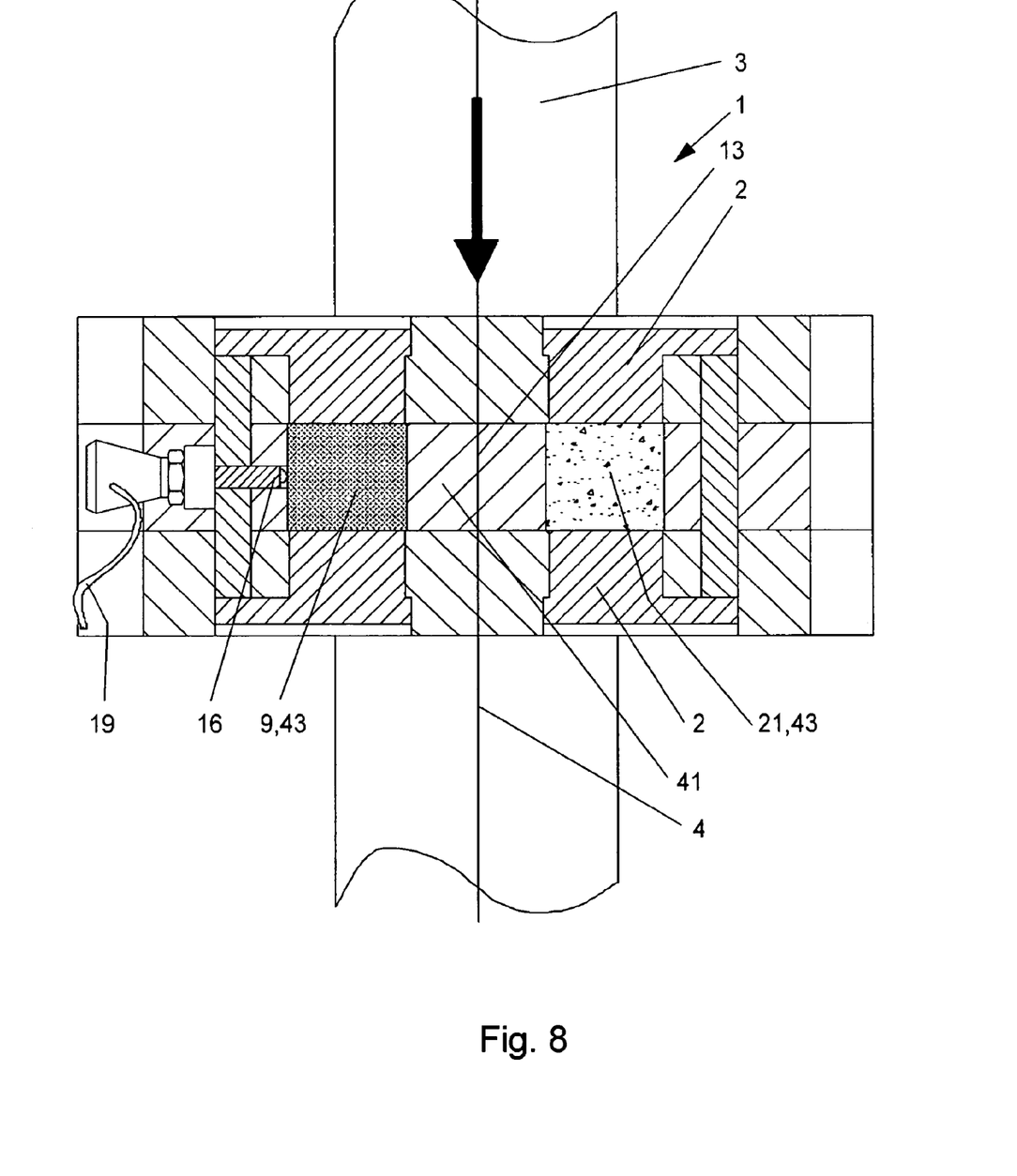
FIG. 8 is a vertical sectional view approximately along line VIII-VIII in FIG. 5.

FIG. 8 illustrates the construction of the apparatus 1 in a vertical sectional view. Only the construction of the housing 2 and the arrangement of the rotary piston 41 in the housing 2 are illustrated. For reasons of better understanding the drawings, the drive for the rotary piston 41 is not illustrated. The same applies to the channels for a cooling medium and a heating medium.

Many variations and modifications may be made to the preferred embodiments of the invention without departing substantially from the spirit and principles of the invention. All such modifications and variations are intended to be included herein within the scope of the present invention, as defined by the following claims.

I claim:

1. An apparatus for determining crystallization solidification curves of a fat-containing mass, comprising:
   a tube section through which a liquid fat-containing mass flows, said tube section defining a removal location from which a sample of the liquid fat-containing mass can be removed;
   a measurement chamber,
      said measurement chamber being connected to said tube section such that the sample of fat-containing mass enters said measurement chamber,
      said measurement chamber including a temperature sensor being designed and arranged to sense the temperature of the sample of fat-containing mass contained in said measurement chamber,
      said measurement chamber including a cooled wall being designed and arranged to solidify the sample of fat-containing mass contained in said measurement chamber,
      said measurement chamber including a movable piston; and
   a melting chamber, said melting chamber being separate from and outside of said tube section and said measurement chamber and comprising a heating unit that heats said melting chamber so as to melt the solidified sample of fat-containing mass when provided within said melting chamber;
   said piston of said measurement chamber being designed and arranged to be moved in a way to transfer the solidified sample of fat-containing mass from said measurement chamber into said melting chamber.

2. The apparatus of claim 1, wherein
   said piston is designed and arranged to oscillate in a linear direction in the sense of a forward stroke directed into said melting chamber and a backward stroke directed out of said melting chamber,
   said melting chamber is designed and arranged to be aligned with said measurement chamber, and
   said melting chamber includes a unit for retaining the solidified sample of fat-containing mass in said melting chamber during the backward stroke of said piston.

3. The apparatus of claim 1, wherein
   said piston is designed as a rotary piston,
   said rotary piston includes at least three chambers, and
   said at least three chambers are designed and arranged to alternately form said measurement chamber, said melting chamber, and said tube section depending on a rotational position of said rotary piston.

4. The apparatus of claim 2, wherein
   said tube section comprises a tube section having an axis, and
   said measurement chamber and said melting chamber are arranged approximately symmetrical with respect to the axis of said tube section.

5. The apparatus of claim 3, wherein
   said tube section comprises a tube section having an axis, and
   said measurement chamber and said melting chamber are arranged approximately symmetrical with respect to the axis of said tube section.

6. The apparatus of claim 1, wherein
   said tube section has a cross-section of flow,
   said melting chamber is designed to be at least partly approximately cylindrical, and
   said melting chamber is at least substantially arranged outside of the cross-section of flow.

7. The apparatus of claim 2, wherein
   said tube section has a cross-section of flow,
   said melting chamber is designed to be at least partly approximately cylindrical, and
   said melting chamber is at least substantially arranged outside of the cross-section of flow.

8. The apparatus of claim 3, wherein
   said tube section has a cross-section of flow,
   said melting chamber is designed to be at least partly approximately cylindrical, and
   said melting chamber is at least substantially arranged outside of the cross-section of flow.

9. The apparatus of claim 2, further comprising a guiding cage, said guiding cage being designed and arranged to assist the transfer of the solidified sample of fat-containing mass from said measurement chamber into said melting chamber.

10. The apparatus of claim 9, wherein
    said measurement chamber has an axis,
    said melting chamber has an axis,
    said guiding cage has an axis,
    the axis of said guiding cage is aligned to the axes of said measurement chamber and said melting chamber,
    said tube section has a cross-section of flow, and
    said guiding cage is arranged in the cross-section of flow.

11. The apparatus of claim 10, wherein said guiding cage is designed as a bush section including openings.

12. The apparatus of claim 1, further comprising
a cooling unit, said cooling unit being connected to said measurement chamber and being designed and arranged to cool the liquid sample of fat-containing mass contained in said measurement chamber to attain a solidified sample of fat-containing mass.

13. The apparatus of claim 2, wherein said unit for retaining the solidified sample of fat-containing mass in said melting chamber during the backward stroke of said piston includes a receiving bush and a retaining element, said retaining element being connected to said receiving bush and being designed and arranged to retain the solidified sample of fat-containing mass in said melting chamber.

14. The apparatus of claim 13, wherein said retaining element is selected from the group consisting of a ball valve, bent knives, and barbed elements.

15. The apparatus of claim 3, wherein
said rotary piston has an axis,
said tube section has an axis,
the axis of said rotary piston is arranged to be parallel to and spaced apart from the axis of said tube section.

16. The apparatus of claim 15, further comprising a housing, said rotary piston being arranged in said housing.

17. The apparatus of claim 16, wherein said temperature sensor is arranged within said housing in a way to be movable into an out off said measurement chamber.

18. The apparatus of claim 1, wherein said fat-containing mass is a chocolate mass.

19. An apparatus for determining crystallization solidification curves of a fat-containing mass, comprising:
a tube section through which a liquid fat-containing mass flows, said tube section defining a removal location from which a sample of the liquid fat-containing mass can be removed;
a measurement chamber,
said measurement chamber being connected to said tube section such that the sample of fat-containing mass enters said measurement chamber,
said measurement chamber including a temperature sensor being designed and arranged to sense the temperature of the sample of fat-containing mass contained in said measurement chamber,
said measurement chamber including a cooled wall being designed and arranged to solidify the sample of fat-containing mass contained in said measurement chamber,
said measurement chamber including a movable piston; and
a melting chamber, said melting chamber being separate from and outside of said tube section and said measurement chamber and comprising a heating unit that heats said melting chamber so as to melt the solidified sample of fat-containing mass when provided within said melting chamber, said melting chamber including a unit for retaining the solidified sample of fat-containing mass in said melting chamber,
said piston of said measurement chamber being designed and arranged to oscillate in a linear direction in the sense of
a forward stroke to transfer the solidified sample of fat-containing mass from said measurement chamber into said melting chamber and
a backward stroke directed out of said melting chamber, said unit for retaining the solidified sample of fat-containing mass in said melting chamber being designed and arranged to retain the solidified sample of fat-containing mass in said melting chamber during the backward stroke of said piston.

20. An apparatus for determining crystallization solidification curves of a fat-containing mass, comprising:
a tube section through which a liquid fat-containing mass flows, said tube section defining a removal location from which a sample of the liquid fat-containing mass can be removed;
a measurement chamber,
said measurement chamber being connected to said tube section such that the sample of fat-containing mass enters said measurement chamber,
said measurement chamber including a temperature sensor being designed and arranged to sense the temperature of the sample of fat-containing mass contained in said measurement chamber,
said measurement chamber including a cooled wall being designed and arranged to solidify the sample of fat-containing mass contained in said measurement chamber,
said measurement chamber including a movable piston, said piston being designed as a rotary piston; and
a melting chamber, said melting chamber being separate from and outside of said tube section and said measurement chamber and comprising a heating unit that heats said melting chamber so as to melt the solidified sample of fat-containing mass when provided within said melting chamber;
said piston of said measurement chamber being designed and arranged to be moved in a way to transfer the solidified sample of fat-containing mass from said measurement chamber into said melting chamber,
said piston including at least three chambers, said at least three chambers being designed and arranged to alternately form said measurement chamber, said melting chamber, and said tube section depending on a rotational position of said rotary piston.

\* \* \* \* \*